(12) United States Patent
Smith et al.

(10) Patent No.: US 11,457,929 B2
(45) Date of Patent: Oct. 4, 2022

(54) SYSTEM, DEVICE AND METHOD FOR TREATMENT OF HEMORRHOIDS

(71) Applicant: BOSTON SCIENTIFIC SCIMED, INC., Maple Grove, MN (US)

(72) Inventors: Paul Smith, Smithfield, RI (US); Tyler Cloyd, Boston, MA (US); Joseph Rausa, Littleton, MA (US); Elizabeth Mark, Boston, MA (US); Jared Robertson, Boston, MA (US); Conor Reid, Cambridge, MA (US); Andrew L. Akers, Framingham, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 16/934,524

(22) Filed: Jul. 21, 2020

(65) Prior Publication Data

US 2021/0022746 A1 Jan. 28, 2021

Related U.S. Application Data

(60) Provisional application No. 62/876,846, filed on Jul. 22, 2019.

(51) Int. Cl.
*A61B 17/128* (2006.01)
*A61B 17/12* (2006.01)
(Continued)

(52) U.S. Cl.
CPC ........ *A61B 17/1285* (2013.01); *A61B 17/122* (2013.01); *A61B 17/12013* (2013.01);
(Continued)

(58) Field of Classification Search
CPC .... A61B 17/12009; A61B 2017/12018; A61B 1/31; A61B 2017/3452; A61B 17/22031; A61B 2017/22034; A61B 17/00818
See application file for complete search history.

(56) References Cited

U.S. PATENT DOCUMENTS 4,226,239 A  10/1980 Polk et al.
4,374,523 A   2/1983 Yoon
(Continued)

FOREIGN PATENT DOCUMENTS

JP   2004 167257   6/2004
WO     01/82847  11/2001
WO   2017/106933   6/2017

*Primary Examiner* — Shaun L David
*Assistant Examiner* — Mitchell Brian Hoag
(74) *Attorney, Agent, or Firm* — Fay Kaplun & Marcin, LLP

(57) ABSTRACT

A device for treating hemorrhoids includes a housing sized and shaped for insertion to a target site within a rectum. The device also includes an inner member received within the housing such that the member may move longitudinally relative to the housing. In addition, the device includes a ligating mechanism at a distal end of the member which includes grasping arms movable between a receiving configuration in which distal ends of the arms are separated from one another and a grasping configuration in which the distal ends are drawn together to grasp tissue. The mechanism includes a ligating band received around the arms that is movable distally off of the arms to constrict around tissue grasped by the arms.

16 Claims, 4 Drawing Sheets

(51) Int. Cl.
*A61B 17/122* (2006.01)
*A61B 17/00* (2006.01)
(52) U.S. Cl.
CPC .............. *A61B 2017/00818* (2013.01); *A61B 2017/12004* (2013.01); *A61B 2017/12018* (2013.01)

(56) References Cited

U.S. PATENT DOCUMENTS

| | | | |
|---|---|---|---|
| 6,152,936 | A * | 11/2000 | Christy et al. ... A61B 17/12013 606/148 |
| 2007/0225734 | A1 | 9/2007 | Bell et al. |
| 2008/0207995 | A1 * | 8/2008 | Kortenbach ....... A61B 18/1445 600/104 |
| 2009/0005647 | A1 * | 1/2009 | Bozdag ................... A61B 1/31 600/235 |
| 2010/0145361 | A1 | 6/2010 | Francischelli et al. |
| 2015/0018848 | A1 * | 1/2015 | Kappel .............. A61B 17/1285 606/140 |
| 2018/0092644 | A1 * | 4/2018 | Wallis ..................... A61B 17/12 |
| 2019/0150930 | A1 * | 5/2019 | Taffa ................. A61B 17/12009 |
| 2019/0298396 | A1 * | 10/2019 | Gamba ................ A61B 17/221 |
| 2021/0007749 | A1 * | 1/2021 | Basu ............... A61B 17/12013 |
| 2021/0093309 | A1 * | 4/2021 | Palermo .............. A61B 17/068 |
| 2021/0236170 | A1 * | 8/2021 | Shashar ................ A61B 5/435 |

* cited by examiner

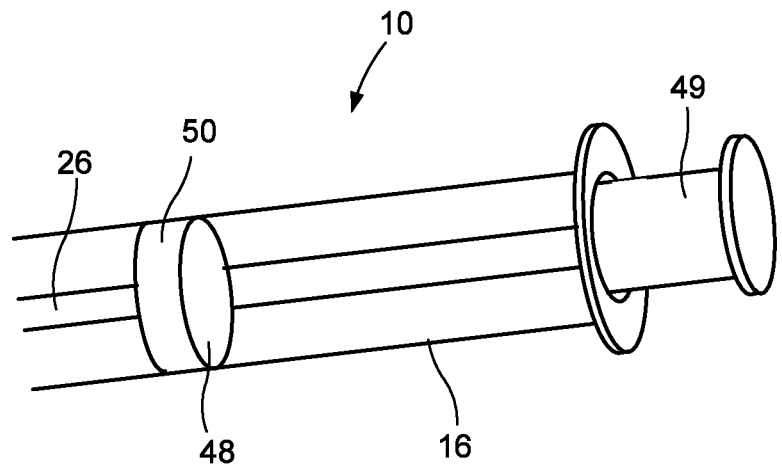
FIG. 4
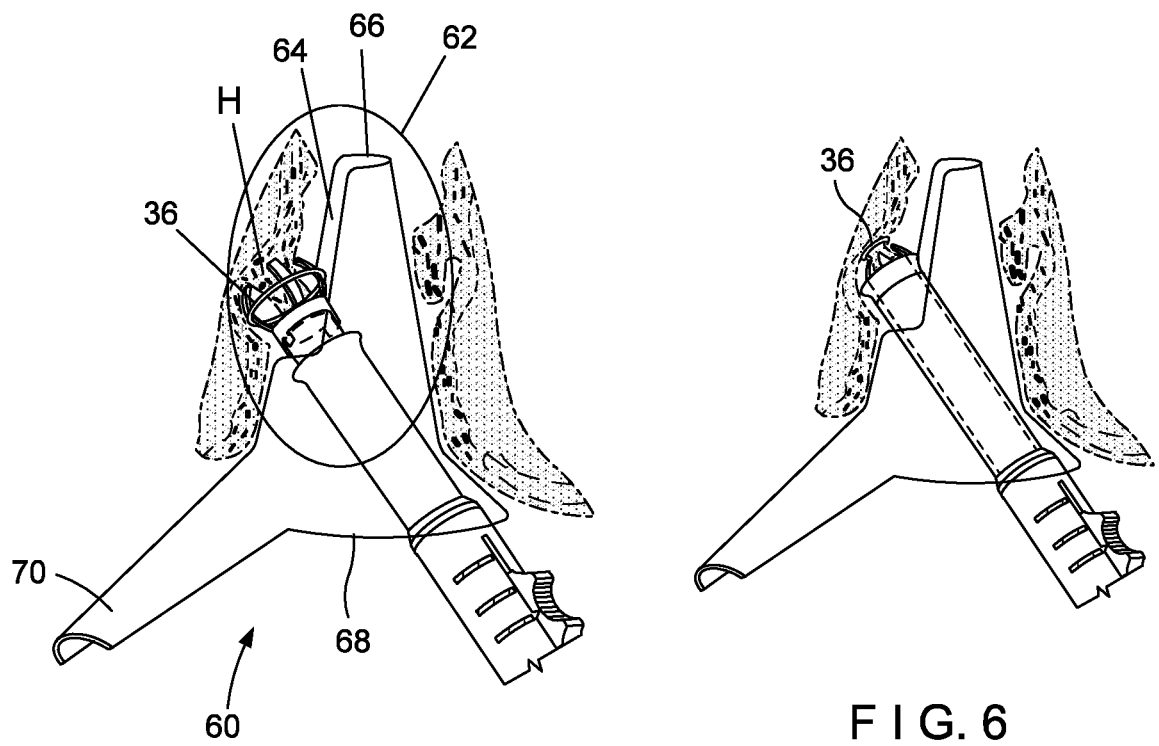
FIG. 5
FIG. 6

SYSTEM, DEVICE AND METHOD FOR TREATMENT OF HEMORRHOIDS

PRIORITY CLAIM

The present disclosure claims priority to U.S. Provisional Patent Application Ser. No. 62/876,846 filed Jul. 22, 2019; the disclosure of which is incorporated herewith by reference.

FIELD

The present disclosure relates generally to devices and methods for treating hemorrhoids and, more specifically, for treating internal hemorrhoids.

BACKGROUND

Hemorrhoids are swollen and inflamed veins around the anus or in the lower rectum. Hemorrhoids may be external, forming under the skin around the anus, or internal, forming in the lining of the anus and the lower rectum.

Internal hemorrhoids are often difficult to treat and certain treatment methods may cause patient discomfort.

SUMMARY

The present disclosure relates to a device for treating internal hemorrhoids. The device includes an elongate housing extending from a proximal end to a distal end sized and shaped for insertion into a living body, the distal end of the housing being configured for insertion to a target site within a rectum; a handle extending from a distal end coupled to the proximal end of the housing to a proximal end, the handle being configured to remain outside the body while the distal end of the housing is inserted into the rectum; and an inner elongate member received within the housing, the housing and elongate member being coupled to one another such that the housing and the elongate member may move longitudinally relative to one another. The device also includes a tissue grasping and ligating mechanism coupled to a distal end of the elongate member, the grasping and ligating mechanism including a plurality of tissue grasping arms movable between a tissue receiving configuration in which distal ends of the grasping arms are separated from one another by a first distance and a tissue grasping configuration in which the distal ends of the grasping arms are drawn together so that they are separated from one another by a second distance smaller than the first distance to grasp tissue received between the grasping arms, the grasping and ligating mechanism further including a ligating band received around the grasping arms, the ligating band being movable distally off of the grasping arms to constrict around tissue grasped by the grasping arms.

In an embodiment, the device further includes a tissue engaging structure pulling tissue proximally away from surrounding tissue between the distal ends of the grasping arms toward a distal end of the elongate member.

In an embodiment, the elongate member defines a lumen extending therethrough, tissue engaging structure including one of a clip, a cork screw, a hook and a grasper.

In an embodiment, the elongate member defines a lumen extending therethrough, the tissue engaging structure includes a source of negative fluid pressure fluidly coupled to a proximal end of the lumen to apply suction to the distal end of the elongate member.

In an embodiment, the source of negative fluid pressure includes a piston slidably mounted within a vacuum chamber formed within the handle, the vacuum chamber being fluidly coupled to the lumen.

In an embodiment, the grasping arms are distributed circumferentially around a longitudinal axis of the elongate member, proximal ends of the grasping arms being separated from the longitudinal axis by a first radial distance, each of the grasping arms extending gradually further from the longitudinal axis from its proximal end to a point of maximum separation from the longitudinal axis and bending back toward the longitudinal axis from the point of maximum separation to its distal end.

In an embodiment, the points of maximum separation of the grasping arms are substantially aligned along the longitudinal axis.

In an embodiment, first and second ones of the grasping arms include a ligating band retaining structure formed thereon at a position at which the ligating band is to be maintained until it is deployed.

In an embodiment, the ligating band retaining structures are located at the point of maximum separation of the first and second grasping arms.

In an embodiment, the housing includes a distal tip gradually increasing in diameter from a first diameter at a proximal end of the distal tip to a maximum diameter at a distal end of the distal tip.

In an embodiment, the ligating band retaining structures are formed as notches in radially outer surfaces of the first and second grasping arms which face away from the longitudinal axis.

In an embodiment, the ligating band retaining structures include at least one of a groove, a protrusion, a textured surface, a hold, a lock and an adhesive.

The present disclosure also relates to a system for treating internal hemorrhoids. The system includes an introducer, extending from a proximal end to a distal end sized and shaped for insertion into an anus, the introducer being transparent for observation of anatomy of the anus, the introducer increasing in diameter from the proximal end to the distal end, the introducer including a slot configured for alignment with a target portion of tissue. The system also includes a device which has an elongate housing extending from a proximal end to a distal end sized and shaped for insertion into a living body through the introducer, the distal end of the housing being configured for insertion to a target site within a rectum; a handle extending from a distal end coupled to the proximal end of the housing to a proximal end, the handle being configured to remain outside the body while the distal end of the housing is inserted into the rectum; and an inner elongate member received within the housing, the housing and elongate member being coupled to one another such that the housing and the elongate member may move longitudinally relative to one another. In addition, the device includes a tissue grasping and ligating mechanism coupled to a distal end of the elongate member, the grasping and ligating mechanism being sized and shaped for insertion through the slot of the introducer and including a plurality of tissue grasping arms movable between a tissue receiving configuration in which distal ends of the grasping arms are separated from one another by a first distance and a tissue grasping configuration in which the distal ends of the grasping arms are drawn together so that they are separated from one another by a second distance smaller than the first distance to grasp tissue received between the grasping arms, the grasping and ligating mechanism further including a ligating band received around the grasping arms, ligating band being movable distally off of the grasping arms to constrict around tissue grasped by the grasping arms.

In an embodiment, the system further includes a handle extending radially outward from the proximal end of the introducer.

In an embodiment, the system further includes a tissue engaging structure pulling tissue proximally away from surrounding tissue between the distal ends of the grasping arms toward a distal end of the elongate member.

In an embodiment, the elongate member defines a lumen extending therethrough, tissue engaging structure including one of a clip, a cork screw, a hook and a grasper.

In an embodiment, the housing includes a distal tip gradually increasing in diameter from a first diameter at a proximal end of the distal tip to a maximum diameter at a distal end of the distal tip.

In addition, the present disclosure includes a method for treating internal hemorrhoids. The method includers inserting into a target site within a rectum, a device comprising an elongate housing extending from a proximal end to a distal end, a handle coupled to the proximal end of the housing, an inner elongate member received within the housing, a tissue grasping and ligating mechanism of the device coupled to a distal end of the elongate member for moving a plurality of tissue grasping arms from a tissue receiving configuration to a tissue grasping configuration; receiving a target portion of tissue within the tissue grasping and ligating mechanism; actuating the tissue grasping and ligating mechanism from the tissue receiving configuration to the tissue grasping configuration; and actuating the elongate housing to push a ligating band off of the device and onto the target portion of tissue.

In an embodiment, the method further includes inserting an introducer into the target site prior to insertion of the device into the target site, wherein the introducer extends from a proximal end to a distal end and includes a slot configured for alignment with the target portion of tissue; inserting the device proximally through the distal end of the introducer; and inserting the grasping and ligating mechanism proximally through the slot of the introducer to engage the target portion of tissue.

In an embodiment, the device includes a source of negative fluid pressure, further comprising, pulling tissue proximally away from surrounding tissue into the tissue grasping and ligating mechanism.

In an embodiment, the device includes tabs located on a proximal end of the grasping and ligating mechanism and slots located on the distal end of the elongate member, further comprising, disengaging the grasping and ligating mechanism from the elongate member by holding the grasping and ligating mechanism while rotating the device, wherein the tabs slide out of the slots, freeing the grasping and ligating mechanism from the device.

BRIEF DESCRIPTION

FIG. 4 shows a partially cut-away view of the handle of the device of FIG. 1 showing a piston mechanism;

FIG. 5 shows a perspective view of a system including the device of FIG. 1 in use in a first step of an exemplary method for treating a hemorrhoid; and FIG. 6 shows a perspective view of a system including the device of FIG. 1 in use in a second step of an exemplary method for treating a hemorrhoid.

DETAILED DESCRIPTION

Figure 1:
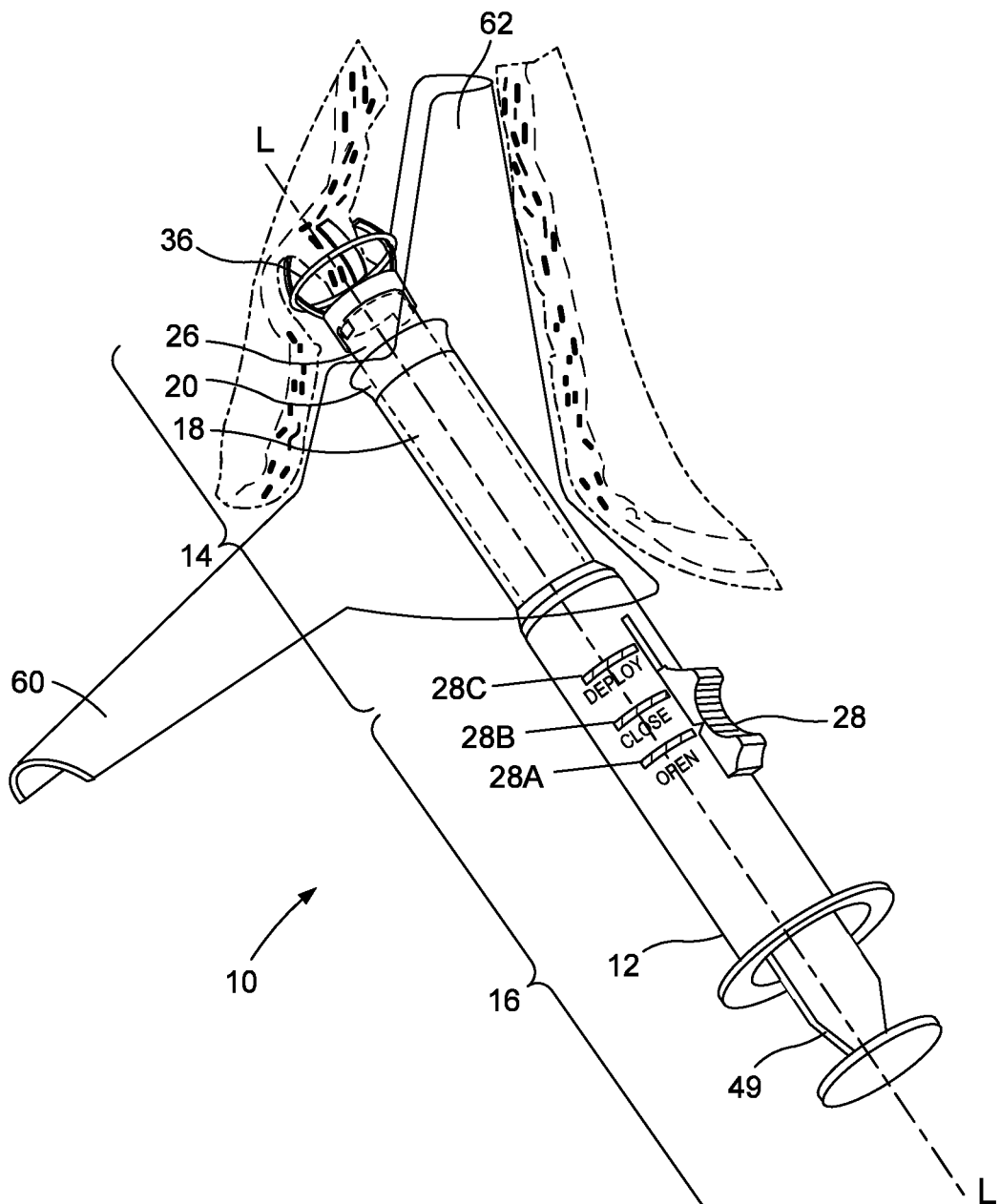
FIG. 1 shows a perspective view of a device for treating hemorrhoids according to a first exemplary embodiment.

The present disclosure may be further understood with reference to the following description and the appended drawings, wherein like elements are referred to with the same reference numerals. The present disclosure is directed to a device and method for treating internal hemorrhoids. It is noted that the terms proximal and distal, as used herein, refer to a direction toward (proximal) and away from (distal) a user of the device. Although the embodiments described herein a specifically configured for the treatment of internal hemorrhoids, those skilled in the art will understand that the embodiments described herein may also be employed to treat similar lesions, such as polyps, that are accessible in the anus.

Figure 2:
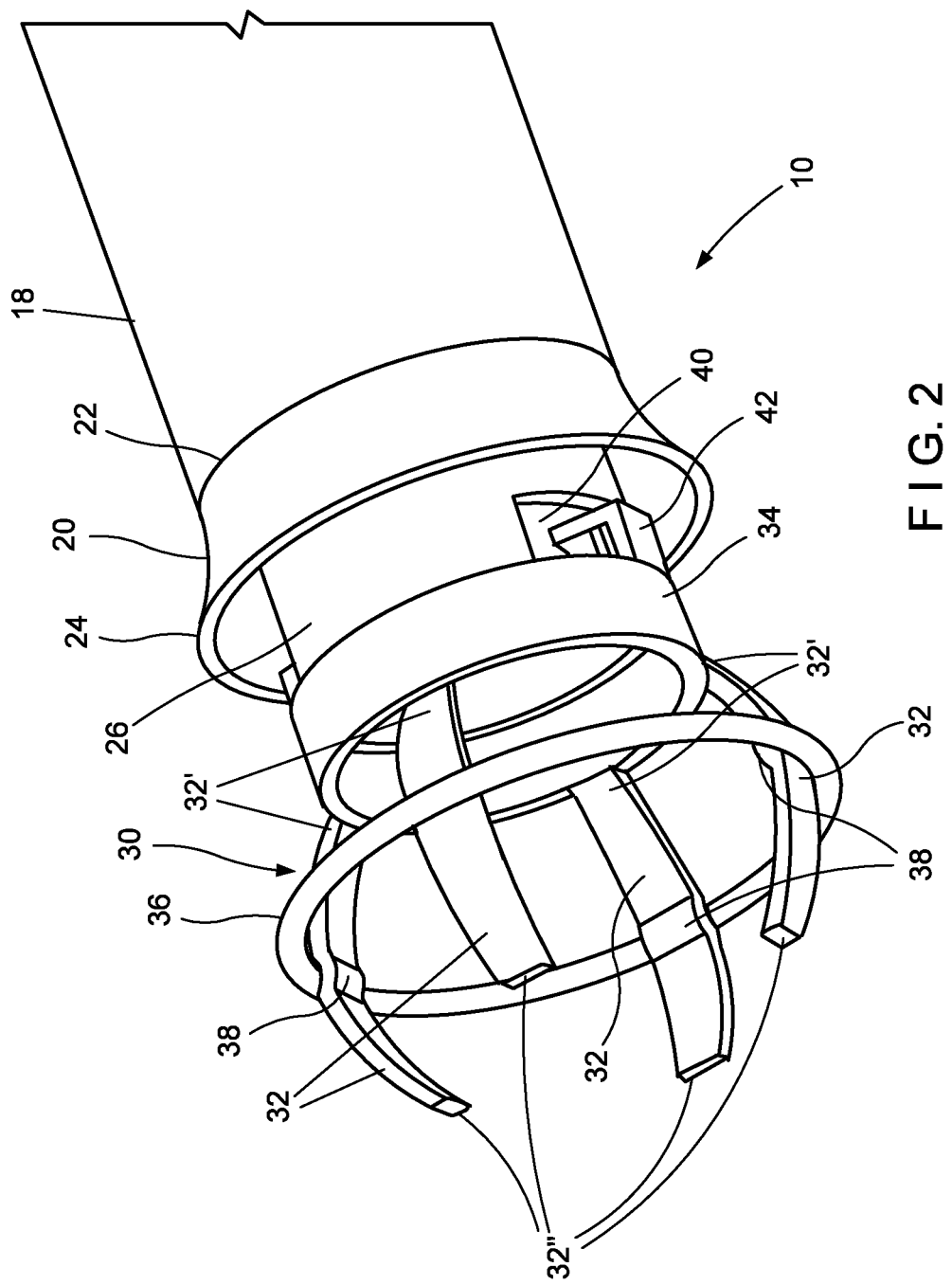
FIG. 2 shows a perspective view of a distal end of the device of FIG. 1 in a first configuration.
Figure 3:
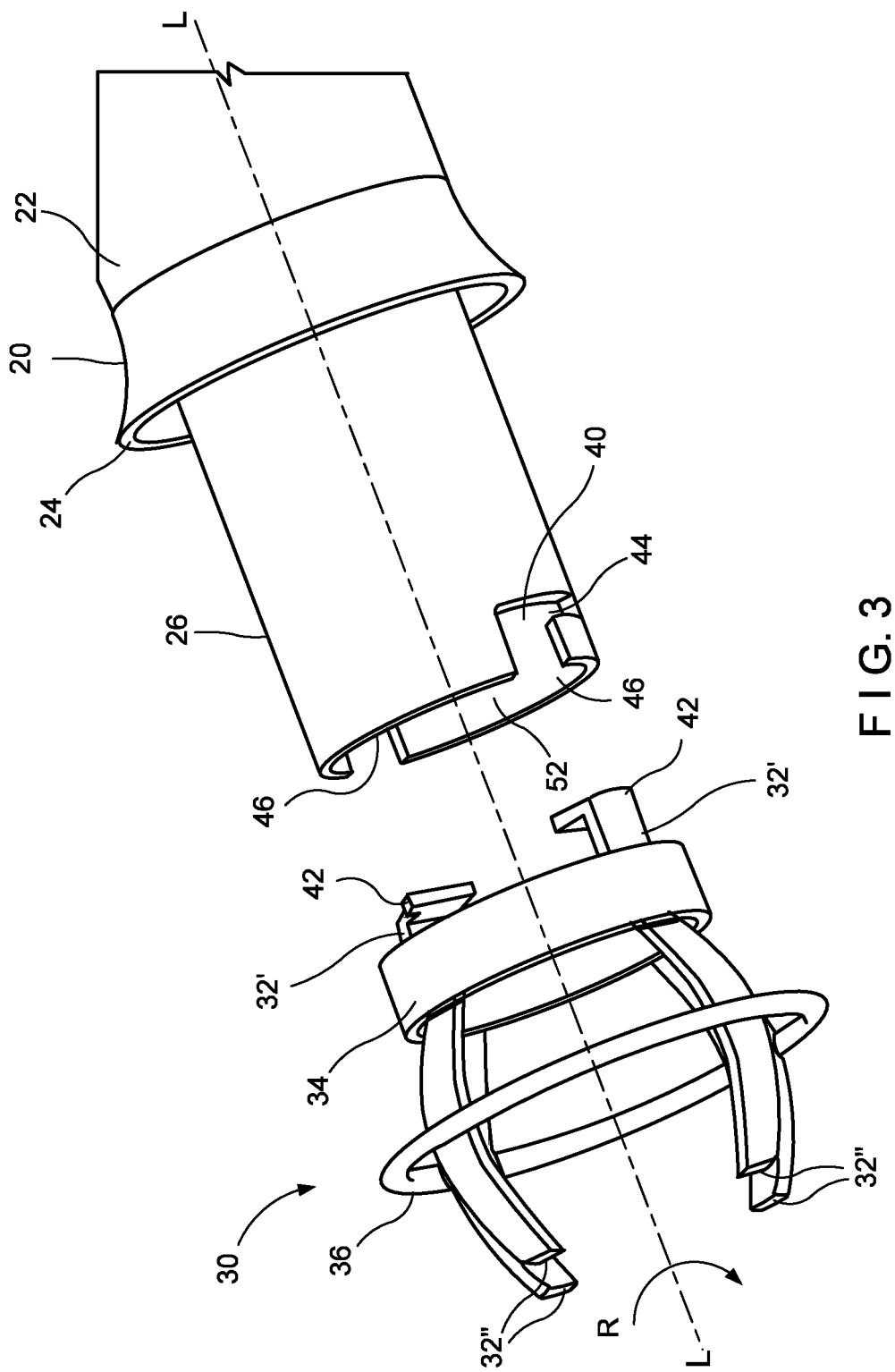
FIG. 3 shows a perspective view of the distal end of the device of FIG. 1 in a second configuration.

As shown in FIGS. 1-3, a device 10 for treating internal hemorrhoids includes a housing 12 including a distal portion 14 sized and shaped for insertion into the anus. The housing 12, in this embodiment, includes a handle 16 which, during use, remains outside the body accessible to the user. The distal portion 14 includes a substantially cylindrical outer housing 18 with a flared distal tip 20. Those skilled in the art will recognize that the outer housing 18 may take any suitably atraumatic shape. For example, the outer housing 18 may have any suitable smooth non-cylindrical outer profile (elliptical, etc.) and the outer housing 18 may have any shape to its flared distal tip 20 so long as the diameter of the outer housing 18 gradually increases toward a distal end thereof so that the distal tip 20 can smoothly engage with grasping arms 32 (se FIG. 2) of the device 10 as will be described in more detail below. The distal tip 20 of the outer housing 18 increases gradually in diameter from a proximal end 22 of the distal tip 20 to a distal end 24 of the distal tip 20.

An inner elongate member 26 extends within the outer housing 18 from the handle 16 to extend distally out of the outer housing 18 distally beyond the distal tip 20. The elongate member 26 is connected to an actuator 28 on the handle 16 via a mechanism that moves the elongate member 26 longitudinally within the outer housing 18 as the actuator is moved distally and proximally relative to the handle 16. Releasably coupled to the distal end of the elongate member 26 is a grasping and ligating mechanism 30. The grasping and ligating mechanism 30 includes a plurality of tissue grasping arms 32 coupled to a radially inner surface of a ring member 34 and arranged around a circumference of the ring member 34. The grasping arms 32 are biased to spread apart from one another radially away from a longitudinal axis L of the grasping and ligating mechanism 30 into a tissue receiving configuration. Although this embodiment shows four grasping arms 32, those skilled in the art will understand that any desired number of arms 32 may be employed with preferably at least three arms 32.

As shown in FIGS. 1-3, the grasping arms 32 of this embodiment are curved with a proximal end of each of the grasping arms 32 being received radially within the ring member 34. This maintains the proximal ends 32' of the grasping arms 32 at a diameter substantially equal to that of the distal end of the elongate member 26. Moving distally away from the proximal ends 32', each of the arms 32 extends away from the axis L to a maximum diameter adjacent to the notches 38. Moving distally from the notches 32, the grasping arms 32 curve back toward the axis L to a minimum diameter at distal ends 32" thereof. In this embodiment, each of the grasping arms 32 is a rigid section that follows an arc that is a portion of a circle so that the grasping arms 32, in the open tissue receiving configuration, collectively define a portion of a sphere.

Those skilled in the art will recognize however that the specific shape of the grasping arms 32 is not limited to this shape and the grasping arms may take any desired shape so long as the grasping arms 32 extend gradually away from the axis L from a proximal end 32' to a point at or slightly distal of band retaining structures described in more detail below. This permits the inner member 26 to be drawn proximally into the outer housing 18 to move the grasping arms 32 gradually from the open tissue receiving configuration to the closed tissue gripping configuration as the outer housing 18 slides distally over the proximal portions of the grasping arms 32. Distally of the band retaining structures, the grasping arms 32 bend back toward the axis L so that, when a ligating band 36 is dislodged from the retaining structures as described below, the bias of the ligating band 36 will interact with a slope formed by the decreasing diameter defined by progressively distal portions of the grasping arms 32 to enable the ligating band 36 to move distally over the grasping arms 32 and slip off of the distal ends 32" of the grasping arms 32 so that it can constrict around tissue immediately distal to the portion of tissue gripped by the grasping arms 32.

As indicated above, a ligating band 36 is received around the grasping arms 32 so that, when the grasping arms 32 are in the tissue receiving configuration as shown in FIG. 2, the ligating band 36 is stretched beyond a resting diameter to which it returns when not constrained by the grasping arms 32. As would be understood by those skilled in the art, any suitably sized known ligating band 36 may be employed and any ligating band 36 for use with these embodiments may include any known therapeutic agent such as medications to treat the ligated tissue and/or to reduce discomfort during the healing process. As also indicated above, each of the grasping arms 32 of this embodiment includes a band retaining structure to retain the ligating band 36 at a desired position on the grasping arms 32 until the user operates the actuator 28 to deploy the ligating band 36. In this embodiment the band retaining structure is a series of notches 38 formed on the grasping arms 32. The notches 38 are sized and shaped to receive the ligating band 36 therein so that the ligating band 36 does not inadvertently slip off of the grasping arms 32 before a user intends to deploy it.

In this embodiment, the notches 38 are located at a point of maximum diameter of a circle circumscribing the grasping arms 32. Those skilled in the art will understand that any number of features may be substituted for or used in conjunction with the notches 38 to maintain the ligating band 36 in position until deployment. For example, the ligating band 36 may be held in place by one or more grooves, one or more protrusions, textured surfaces, a locking feature, adhesive, etc.) and that the band retaining structures may be on all or only a subset of the grasping arms 32. In addition, those skilled in the art will understand that, although this embodiment is shown with the handle 16, the outer housing and the elongate member 26 arranged longitudinally along a common axis L, the distal portion of the device may be angled relative to the handle 16 to any desired extent to, for example, facilitate reaching hemorrhoids in different locations within the body.

The grasping and ligating mechanism 30 of this embodiment is releasably coupled to the distal end of the elongate member 26 via two slots 40 formed in the elongate member 26 each of which is sized and shaped to receive a tab 42 extending radially inward toward the axis L from the proximal ends of first and second ones of the grasping arms 32. Each slot 40 is generally L shaped and includes a first portion 44 extending circumferentially around a portion of the elongate member 26 and opening into a second part 46 extending distally from the first portion 44 to an open distal end. When the grasping and ligating mechanism 30 is coupled to the elongate member 26, the tabs 42 are received in the first portions 44 of the slots 40 and rotated away from the second portions 46 so that the tabs 42 are retained in the slots 40 and the grasping and ligating mechanism 30 remains coupled to the elongate member 26. Those skilled in the art will understand that this allows a user of the device 10 to select one from a variety of types and/or sizes of grasping and ligating mechanisms 30 depending on the characteristics of the anatomy being addressed by the user.

As shown in FIG. 1, the handle 16 also includes a piston 48 slidable within a vacuum chamber 50 formed within the handle 16 so that, drawing the piston 48 (e.g., plunger) proximally through the vacuum chamber 50 draws a vacuum in the vacuum chamber 50. The piston 48 is coupled to a pull lever 49 that extends proximally from the handle 16 so that it is accessible to the user. A proximal end of the elongate member 26 is in fluid communication with the vacuum chamber 50 so that, as a vacuum is drawn in the vacuum chamber 50, suction is applied to the distal end of the elongate member 26 via a lumen 52 extending through the elongate member 26. Those skilled in the art will recognize that any source of negative fluid pressure may be substituted for or added to the disclosed piston mechanism including, for example, a syringe, bulb, pump or via a tube extending to a secondary source of negative fluid pressure. Furthermore, in addition to or as an alternative to the use of suction to draw tissue into the device 10, any known mechanical tissue grasping mechanisms such as a clip, spiral, cork screw member, hook, grasper, etc. may be used to draw in the tissue as desired.

The user operates the actuator 28 to move the grasping and ligating mechanism 30 from the open tissue receiving configuration (position 28A) to a tissue grasping configuration (actuator position 28B) in which the distal ends of the grasping arms 32 are drawn together toward the axis L by drawing the elongate member 26 proximally into the outer housing 18 (as the user correspondingly advances the handle 16 and outer member 18 distally over the elongate member 26). This allows the grasping arms 32 and the gripped tissue to remain stationary as the outer housing 18 slides distally over the elongate member 26. As the actuator 28 is advanced from position 28A to 28B, the flared distal tip 20 of the outer housing 18 slides over the curved proximal ends of the grasping arms 32. As the distal tip 20 slides over the grasping arms 32 and the more proximal, gradually smaller diameter portions of the distal tip 20 approach and slide over the increasing diameter of the circle formed by the grasping arms 32, the grasping arms 32 are squeezed together forcing the distal ends of the grasping arms 32 toward one another to grip tissue received therebetween.

In this embodiment, it is desired that, in the tissue grasping configuration, the distal ends of the grasping arms 32 remain separated from one another by a gap corresponding to diameter of a portion of tissue to be encircled by the ligating band 36. For example, the gap may be between approximately 3 mm-15 mm depending on the size of the hemorrhoid being targeted. Those skilled in the art will understand that this gap may be made of any desired size or may be eliminated so that the distal ends of the arms 32 touch one another when in the tissue grasping configuration. When the grasping arms 32 have been moved to the closed tissue grasping configuration and the user confirms that the desired portion of tissue has been grasped by the grasping arms 32 (e.g., a target hemorrhoid and a suitable margin of surrounding healthy tissue), the user may deploy the ligating band 36 by moving the actuator 28 to position 28C. This draws the elongate member 26 further proximally into the outer housing 18 until the distal tip 20 of the outer housing 18 slides distally past the notches 38 moving the ligating band out of the notches 38 beyond the point of maximum diameter of the grasping arms 32. As described above, the ligating band 36 then constricts and moves under its own bias distally over the distal portions of the grasping arms 32 until the ligating band 36 slips off of the distal ends 32" of the grasping arms 32 and constricts around the target tissue.

A user may disengage the grasping and ligating mechanism 30 from the elongate member 26 by holding the grasping and ligating mechanism 30 while rotating the device 10 in the direction of the arrow R. As the grasping and ligating mechanism 30 is held in place, the tabs 42 will slide through the first portions 44 of the slots 40 to the second portions 46. The tabs 42 may then slide out of the slots 40 via the second portions 46 freeing the grasping and ligating mechanism 30 from the device 10. The user may then attach a different grasping and ligating mechanism 30 (e.g., a differently sized mechanism 30, a mechanism 30 with a different medication on the ligating band 36, etc.) to the device 10 by reversing this process.

Alternatively, the user may use the detaching feature to replace a grasping and ligating mechanism 30 from which the ligating band 36 has been deployed with a new grasping and ligating mechanism 30 so that the user may repeat the above process and use the same device 10 to treat another hemorrhoid. In single use devices or to provide differently sized or configured grasping and ligating mechanisms 30, the grasping and ligating mechanism 30 may be permanently coupled to the elongate member 26. In this embodiment, the device 10 is a single use device (i.e., for use in a single patient during a single procedure even if the device 10 is used to deploy multiple ligating bands 36 during this single procedure).

In use, as shown in FIGS. 5 and 6, the device 10 is inserted into the anus via a previously inserted introducer 60. The introducer 60 includes a generally conical distal portion 62 formed of transparent plastic with an open slot 64 extending to an open distal end 66. A lip 68 extends radially outward from a proximal end of the conical distal portion 62 to define a point of maximal insertion of the introducer 60 into the body. The introducer 60 also includes a handle 70 extending proximally from the lip 68 and radially outward from the conical distal portion 62 to facilitate positioning and rotation of the introducer 60 as desired within the anus. In this case, the introducer 60 is positioned so that the slot 64 aligns with a hemorrhoid H to be treated and the device 10 is inserted through the introducer 60 until the grasping and ligating mechanism 30 is adjacent to the hemorrhoid H as shown in FIG. 5. As it is drawn toward the hemorrhoid H, the grasping and ligating mechanism 30 is maintained in the open tissue receiving configuration and the device 10 is positioned so that the distal ends of the grasping arms 32 rest on tissue surrounding the hemorrhoid H.

The user then draws the pull lever 49 proximally out of the handle 16 to draw the piston 48 proximally through the vacuum chamber 50 which, in turn, applies suction at the distal end of the elongate member 26 to draw the hemorrhoid H through the grasping and ligating mechanism 30 into the distal end of the elongate member 26. The user may continue to apply suction until the entire hemorrhoid and a margin of surrounding healthy tissue has been drawn between the grasping arms 32. In an embodiment, an anoscope can be used for visualization of the anus wherein the device 10 is inserted through a working channel of the anoscope into the anus.

The user then pushes the outer housing 18 distally over the elongate member 26 and the grasping and ligating mechanism 30 to push the grasping arms 32 toward one another further drawing the tissue surrounding the hemorrhoid H into the device 10. The user may then position the grasping arms 32 so that they are over the tissue surrounding the hemorrhoid H and continue to push the outer housing 18 distally over the grasping arms 32 until the inner surface of the distal tip 20 contacts the ligating band 36 and pushes the ligating band 36 distal out of the notches 38 freeing the ligating band 36 to contract and roll off of the grasping arms 32 to constrict around the tissue immediately distal of the distal ends of the grasping arms 32. The combination of the vacuum applied via the piston 48 and the pulling by the grasping arms 32 enables a user of this device to preferably draw the entire hemorrhoid H into the grasping and ligating mechanism 30 so that the ligating band 36 constricts about healthy tissue surrounding the hemorrhoid H and not over the tissue of the hemorrhoid H itself. This may reduce patient discomfort during healing.

Those skilled in the art will understand that there are various modifications that may be made to the embodiments described without departing from the teachings of this application. For example, although the embodiments have been described in regard to the treatment of internal hemorrhoids, those skilled in the art will understand that the embodiments described herein may also be employed to treat similar lesions, such as polyps.

The invention claimed is:
1. A device for treating internal hemorrhoids, comprising:
an elongate housing extending from a proximal end to a distal end sized and shaped for insertion into a living body, the distal end of the housing being configured for insertion to a target site within a rectum;
a handle extending from a distal end coupled to the proximal end of the housing to a proximal end, the handle being configured to remain outside the body while the distal end of the housing is inserted into the rectum;
an inner elongate member received within the housing, the housing and elongate member being coupled to one another such that the housing and the elongate member may move longitudinally relative to one another; and
a tissue grasping and ligating mechanism coupled to a distal end of the elongate member, the grasping and ligating mechanism including a plurality of tissue grasping arms movable between a tissue receiving configuration in which distal ends of the grasping arms are separated from one another by a first distance and a tissue grasping configuration in which the distal ends of the grasping arms are drawn together so that they are separated from one another by a second distance smaller than the first distance to grasp tissue received between the grasping arias, the grasping and ligating mechanism further including a ligating band received around the grasping arms at a first position on the grasping arms, the ligating band being movable distally off of the grasping arms to constrict around tissue grasped by the grasping arms, wherein the housing is slidable distally over the elongate member and proximal ends of the grasping arms so that the distal end of the housing contacts the ligating band and pushes the ligating band distally out of the first position, wherein the grasping arms are distributed circumferentially around a longitudinal axis of the elongate member, proximal ends of the grasping arms being separated from the longitudinal axis by a first radial distance, each of the grasping arms extending gradually further from the longitudinal axis from its proximal end to a point of maximum separation from the longitudinal axis and bending back toward the longitudinal axis from the point of maximum separation to its distal end, and wherein first and second ones of the grasping arms include a ligating band retaining structure formed thereon at the first position at which the ligating band is to be maintained until it is deployed.

2. The device of claim 1, further comprising a tissue engaging structure configured to pull tissue proximally away from surrounding tissue between the distal ends of the grasping arms toward a distal end of the elongate member.

3. The device of claim 2, wherein the elongate member defines a lumen extending therethrough, the tissue engaging structure including one of a clip, a cork screw, a hook and a grasper.

4. The device of claim 2, wherein the elongate member defines a lumen extending therethrough, the tissue engaging structure includes a source of negative fluid pressure fluidly coupled to a proximal end of the lumen to apply suction to the distal end of the elongate member.

5. The device of claim 4, wherein the source of negative fluid pressure includes a piston slidably mounted within a vacuum chamber formed within the handle, the vacuum chamber being fluidly coupled to the lumen.

6. The device of claim 1, wherein the points of maximum separation of the grasping arms are substantially aligned along the longitudinal axis.

7. The device of claim 1, wherein the ligating band retaining structures are located at the point of maximum separation of the first and second grasping arms.

8. The device of claim 1, wherein the housing includes a distal tip gradually increasing in diameter from a first diameter at a proximal end of the distal tip to a maximum diameter at a distal end of the distal tip.

9. The device of claim 1, wherein the ligating band retaining structures are formed as notches in radially outer surfaces of the first and second grasping anus which face away from the longitudinal axis.

10. The device of claim 1, wherein the ligating band retaining structures include at least one of a groove, a protrusion, a textured surface, a hold, a lock and an adhesive.

11. The device of claim 1, wherein the first position on the grasping arms comprises the point of maximum separation and, when the distal end of the housing pushes the ligating band distally out of the first position, the ligating band contracts and moves distally off of the grasping arms to constrict around the tissue grasped by the grasping arms.

12. A system for treating internal hemorrhoids, comprising:

an introducer, extending from a proximal end to a distal end sized and shaped for insertion into an anus, the introducer being transparent for observation of anatomy of the anus, the introducer including a slot configured for alignment with a target portion of tissue; and a device including:

an elongate housing extending from a proximal end to a distal end sized and shaped for insertion into a living body through the introducer, the distal end of the housing being configured for insertion to a target site within a rectum;

a handle extending from a distal end coupled to the proximal end of the housing to a proximal end, the handle being configured to remain outside the body while the distal end of the housing is inserted into the rectum;

an inner elongate member received within the housing, the housing and elongate member being coupled to one another such that the housing and the elongate member may move longitudinally relative to one another; and a tissue grasping and ligating mechanism coupled to a distal end of the elongate member, the grasping and ligating mechanism being sized and shaped for insertion through the slot of the introducer and including a plurality of tissue grasping arms movable between a tissue receiving configuration in which distal ends of the grasping arms are separated from one another by a first distance and a tissue grasping configuration in which the distal ends of the grasping arms are drawn together so that they are separated from one another by a second distance smaller than the first distance to grasp tissue received between the grasping arms, the grasping and ligating mechanism further including a ligating hand received around the grasping arms, ligating band being movable distally off of the grasping arms to constrict around tissue grasped by the grasping arms, wherein the grasping arms are distributed circumferentially around a longitudinal axis of the elongate member, proximal ends of the grasping arms being separated from the longitudinal axis by a first radial distance, each of the grasping arms extending gradually further from the longitudinal axis from its proximal end to a point of maximum separation from the longitudinal axis and bending back toward the longitudinal axis from the point of maximum separation to its distal end, and wherein first and second ones of the grasping arms include a ligating band retaining structure formed thereon at the first position at which the ligating band is to be maintained until it is deployed.

13. The system of claim 12, further comprising:

a handle extending radially outward from the proximal end of the introducer.

14. The system of claim 12, further comprising:

a tissue engaging structure configured to pull tissue proximally away from surrounding tissue between the distal ends of the grasping arms toward a distal end of the elongate member.

15. The system of claim 14, wherein the housing includes a distal tip gradually increasing in diameter from a first diameter at a proximal end of the distal tip to a maximum diameter at a distal end of the distal tip.

16. The system of claim 14, wherein the introducer increases in diameter from the proximal end to the distal end.

\* \* \* \* \*